United States Patent [19]

Skubitz et al.

[11] Patent Number: 5,266,328
[45] Date of Patent: Nov. 30, 1993

[54] LAMININ A CHAIN POLYPEPTIDES FROM THE CARBOXY TERMINAL GLOBULAR DOMAIN

[75] Inventors: Amy P. N. Skubitz; Leo T. Furcht, both of Minneapolis, Minn.

[73] Assignee: Regents of the University of Minnesota, Minneapolis, Minn.

[21] Appl. No.: 573,672

[22] Filed: Aug. 27, 1990

[51] Int. Cl.$^5$ .................. A61F 2/16; A61F 2/06; A61F 37/10; C07K 5/04
[52] U.S. Cl. ................. 424/427; 424/422; 424/423; 514/1; 514/2; 514/8; 530/326; 530/327; 530/395; 623/4; 623/6
[58] Field of Search .......... 424/422, 423, 427; 514/1, 2, 8; 530/326, 327, 395; 623/4, 6

[56] References Cited

U.S. PATENT DOCUMENTS

| | | | |
|---|---|---|---|
| 4,565,789 | 1/1986 | Liotta et al. | 436/504 |
| 4,578,079 | 3/1986 | Ruoslahti et al. | 623/11 |
| 4,870,160 | 9/1989 | Charonis et al. | 530/326 |
| 5,007,925 | 4/1991 | Tsilibary et al. | 623/1 |

OTHER PUBLICATIONS

"Synthetic Laminin B1 Chain Fragment as Cell Adhesive for Coating Prosthetic Devices and Culture Substrate", Charonis, Pharmaceuticals, 63–7, 1990.
Ohno et al., *Conn. Tiss. Res.*, 15, 199–207 (1986).
Hunter et al., *Nature*, 338, 229–234 (1989).
Timpl et al., *J. Biol. Chem.*, 254, 9933–9937 (1979).
Timpl and Dziadek, *Intern. Rev. Exp. Path.*, 29, 1–112 (1986).
Sasaki et al., *J. Biol. Chem.*, 263, 16536–16544 (1988).
Engel et al., *J. Mol. Biol.*, 150, 97–120 (1981).
Ott et al., *Eur. J. Biochem.*, 123, 63–72 (1982).
Skubitz et al., *J. Biol. Chem.*, 263, 4861–4868 (1988).
Edgar et al., *EMBO J.*, 3, 1463–1468 (1984).
Engvall et al., *J. Cell Biol.*, 103, 2457–2465 (1986).
Goodman et al., *J. Cell Biol.*, 105, 589–598 (1987).
Yurchenco et al., *J. Biol. Chem.*, 260, 7636–7644 (1985).
Timpl et al., *J. Biol. Chem.*, 258, 8922–8927 (1983).
Rao et al., *Biochem. Biophys. Res. Commun.*, 111, 804–808 (1983).
Lesot et al., *EMBO J.*, 2, 861–865 (1983).
Malinoff and Wicha, *J. Cell Biol.*, 96, 1475–1479 (1983).
Terranova et al., *Proc. Natl. Acad. Sci. USA*, 80, 444–448 (1983).
Barsky et al., *Breast Cancer Res. Treat.*, 4, 181188 (1984).
von der Mark and Kuhl, *Biochim. Biophys. Acta*, 823, 147–160 (1985).
Wewer et al., *Proc. Natl. Acad. Sci. USA*, 83, 7137–7141 (1986).
Hinek et al., *J. Cell Biol.*, 105, 138a (1987).
Yoon et al., *J. Immunol.*, 138, 259–265 (1987).
Smalheiser and Schwartz, *Proc. Natl. Acad. Sci. USA*, 84, 6457–6461 (1987).
Yannariello-Brown et al., *J. Cell Biol.*, 106, 1773–1786 (1988).
Mercurio and Shaw, *J. Cell Biol.*, 107, 1873–1880 (1988).
Kleinman et al., *Proc. Natl. Acad. Sci. USA*, 85, 1282–1286 (1988).
Hall et al., *J. Cell Biol.*, 107, 687–697 (1988).
Clegg et al., *J. Cell Biol.*, 107, 699–705 (1988).
Gehlsen et al., *Science*, 241, 1228–1229 (1988).
Horwitz et al., *J. Cell Biol.*, 101, 2134–2144 (1985).
Sonnenberg et al., *Nature*, 336, 487–489 (1988).
Tomaselli et al., *J. Cell Biol.*, 105, 2347–2358 (1987).
Tomaselli et al., *J. Cell Biol.*, 107, 1241–1252 (1988).
Barlow et al., *EMBO J.*, 3, 2355–2362 (1984).

(List continued on next page.)

Primary Examiner—Thurman K. Page
Assistant Examiner—C. Azpuru
Attorney, Agent, or Firm—Merchant, Gould, Smith, Edell, Welter & Schmidt

[57] ABSTRACT

Polypeptides derived from the G domain of the A chain of laminin and having sequences of at least about 5 amino acids, and which exhibit heparin/glycosaminoglycan binding, cell adhesion and cell spreading capacity are described.

Medical devices such as prosthetic implants, percutaneous devices and cell culture substrates coated with a composition including the described polypeptides are also provided.

21 Claims, 15 Drawing Sheets

OTHER PUBLICATIONS

Sasaki et al., *Proc. Natl. Acad. Sci. USA*, 84, 935–939 (1987).
Sasaki and Yamada et al., *J. Biol. Chem.*, 262, 17111–17117 (1987).
Pikkarainen et al., *J. Biol. Chem.*, 262, 10454–10462 (1987).
Pikkarainen et al., *J. Biol. Chem.*, 263, 6751–6758 (1988).
Hartl et al., *Eur. J. Biochem.*, 173, 629–635 (1988).
Graf et al., *Cell*, 48, 989–996 (1987a).
Graf et al., *Biochemistry*, 26, 6896–6900 (1987b).
Kouzi-Koliakos et al., *J. Biol. Chem.*, 264, 17971–17978 (1989).
Koliakos et al., *J. Cell Biol.*, 109, 200a (1989).
Grant et al., *Cell*, 58, 933–943 (1989).
Tashiro et al., *J. Biol. Chem.*, 264, 16174–16182 (1989).
Sephel et al., *Biochem. Biophys. Res. Commun.*, 162, 821–829 (1989).
Liotta, *Am. J. Path.*, 117, 339–348 (1984).
McCarthy et al., *Cancer Met. Rev.*, 4, 125–152 (1985).
Charonis et al., *J. Cell Biol.*, 107, 1253–1260 (1988).
Stewart and Young, *Solid Phase Peptide Synthesis*, Pierce Chemical Co. Pub., Rockford, Ill. (2d ed., 1984).
Hewick et al., *J. Biol. Chem.*, 256, 7990–7997 (1981).
Palm and Furcht *J. Cell Biol.*, 96, 1218–1226 (1983).
Herbst et al., *J. Cell Biol.*, 106, 1365–1373 (1988).
McCarthy et al., *J. Cell Biol.*, 102, 179–188 (1980).
Skubitz et al., *Exp. Cell Res.*, 173, 349–360 (1987).
McCarthy et al., *J. Natl. Cancer Inst.*, 80, 108–116 (1988).
Charonis et al., *J. Cell Biol.*, 100, 1848–1853 (1985).
G. W. Laurie et al., *J. Mol. Biol.*, 189, 205–216 (1986).
Charonis et al., *J. Cell Biol.*, 103, 1689–1697 (1986).
Roberts et al., *Proc. Natl. Acad. Sci. USA*, 82, 1306–1310 (1985).
Shotton et al., *J. Mol. Biol.*, 131, 303–329 (1979).
Furcht et al., *Bio. Mol. Gen. Cancer Met.;* K. Lapis et al., Eds. (1985) 43–53.
Kennedy et al., *J. Cell Phys.*, 114, 257–262 (1983).
Kyte and Doolittle, *J. Mol. Biol.*, 157, 105–132 (1982).
Clement et al., *J. Cell Biol.*, 110, 185–192 (1990).
Schittny and Yurchenco, *J. Cell Biol.*, 110, 825–832 (1990).
Kanemoto et al., *Proc. Natl. Acad. Sci. USA*, 87, 2279–2283 (1990).
Tsilibary and Charonis, *J. Cell Biol.*, 103, 388a (1986).
Mecham et al., *J. Biol. Chem.*, 264, No. 28, 16652–16657 (1989).
Mecham et al., *Biochemistry*, 28, 3716–3722 (1989).

FIG. 13

LAMININ A CHAIN POLYPEPTIDES FROM THE CARBOXY TERMINAL GLOBULAR DOMAIN

GOVERNMENT SUPPORT

This invention was made with government support under contract No. CA-29995 by the U.S. National Institutes of Health. The government has certain rights in the invention.

BACKGROUND OF THE INVENTION

The adhesion of mammalian cells to the extra-cellular matrix is of fundamental importance in regulating growth, adhesion, motility and the development of the proper cellular phenotype. This has implications for normal cell growth and development, wound healing, chronic inflammatory diseases, diabetes, tumor metastasis, and as a delivery mechanism for heparin binding molecules or drugs. Evidence accumulated over the last several years suggests that the molecular basis for the adhesion of both normal and transformed or malignant cells is complex and probably involves several distinct cell surface molecules. Extracellular matrices consist of three types of macromolecules: collagenous glycoproteins, proteoglycans and noncollagenous glycoproteins.

One noncollagenous adhesive glycoprotein of interest is laminin. Laminin likely is one of a multigene family of related molecules [Ohno et al., *Conn. Tiss. Res.*, 15, 199-207 (1986); Hunter et al., *Nature*, 338, 229-234 (1989)]. Laminin is a high molecular weight (approximately 850,000; from the mouse Engelbreth-Holm-Swarm tumor) extracellular matrix glycoprotein found almost exclusively in basement membranes. [Timpl et al., *J. Biol. Chem.*, 254, 9933-9937 (1979)]. Basement membranes are an ubiquitous, specialized type of extracellular matrix separating organ parenchymal cells from interstitial collagenous stroma. Interaction of cells with this matrix is an important aspect of both normal and neoplastic cellular processes. Normal cells appear to require an extracellular matrix for survival, proliferation, and differentiation, while migratory cells, both normal and neoplastic, must traverse the basement membrane in moving from one tissue to another.

Laminin isolated from the Engelbreth-Holm-Swarm murine tumor consists of three different polypeptide chains: B1 with 215,000 MW, B2 with 205,000 MW and A with 400,000 MW [Timpl and Dziadek, *Intern. Rev. Exp. Pat.*, 29, 1-112 (1986)]. When examined at the electron microscopic level with the technique of rotary shadowing, it appears as an asymmetric cross, with three short arms 37 nm long {the lateral short arms having two globular domains and the upper short arm having three globular domains [Sasaki et al., *J. Biol. Chem.*, 263, 16536-16544 (1988)]}, and one long arm 77 nm long, exhibiting a large terminal globular domain [Engel et al., *J. Mol. Biol.*, 150, 97-120 (1981)]. The three chains are associated via disulfide and other chemical bonds. Structural data shows that laminin is a very complex and multidomain protein with unique functions present in specific domains.

Laminin is a major component of basement membranes and is involved in many functions. Laminin has the ability to bind to other basement membrane macromolecules and therefore contributes to the structural and perhaps functional characteristics of basement membranes.

Laminin promotes the adhesion and spreading of a multitude of cells and binds a variety of proteoglycans [Timpl and Dziadek, supra (1986)]. Studies utilizing enzymatic digests of laminin or monoclonal antibodies raised against laminin have defined some of the biologically active regions of the 400 kD A chain of laminin. Its large carboxy-terminal globular domain binds heparin [Ott et al., *Eur. J. Biochem.*, 123, 63-72 (1982); Skubitz et al., *J. Biol. Chem.*, 263, 4861-4868 (1988)], while neurite cell outgrowth and cell adhesion is localized to the region directly above this globule [Edgar et al., *EMBO J.*, 3, 1463-1468 (1984); Engvall et al., *J. Cell Biol.*, 103, 2457-2465 (1986); Goodman et al., *J. Cell Biol.*, 105, 589-598 (1987)]. In addition, the amino terminal globular domain at the top of the molecule is involved in laminin-laminin self assembly [Yurchenco et al., *J. Biol. Chem.*, 260, 7636-7644 (1985)] and the adhesion of hepatocytes [Timpl et al., *J. Biol. Chem.*, 255, 8922-8927 (1983)].

Another important feature of laminin is its ability to associate with cell surface molecular receptors and consequently modify cellular phenotype in various ways. Receptors for laminin ranging in molecular size from 55 to 180 kD have been isolated from a variety of normal and malignant cell lines [Rao et al., *Biochem. Biophys. Res. Commun.*, 111, 804-808 (1983); Lesot et al., *EMBO J.*, 2, 861-865 (1983); Malinoff and Wicha, *J. Cell Biol.*, 96, 1475-1479 (1983); Terranova et al., *Proc. Natl. Acad. Sci. USA*, 80, 444-448 (1983); Barsky et al., *Breast Cancer Res. Treat.*, 4, 181-188 (1984); von der Mark and Kühl, *Biochim. Biophys. Acta.*, 823, 147-160 (1985); Wewer et al., *Proc. Natl. Acad. Sci. USA*, 83, 7137-7141 (1986); Hinek et al., *J. Cell Biol.*, 105, 138a (1987); Yoon et al., *J. Immunol.*, 138, 259-265 (1987); Smalheiser and Schwartz, *Proc. Natl. Acad. Sci. USA*, 84, 6457-6461 (1987); Yannariello-Brown et al., *J. Cell Biol.*, 106, 1773-1786 (1988); Mercurio and Shaw, *J. Cell Biol.*, 107, 1873-1880 (1988); Kleinman et al., *Proc. Natl. Acad. Sci. USA*, 85, 1282-1286 (1988); Hall et al., *J. Cell Biol.*, 107, 687-697 (1988); Clegg et al., *J. Cell Biol.*, 107, 699-705 (1988)]. In the case of human glioblastoma cells [Gehlsen et al., *Science*, 241, 1228-1229 (1988)], several chicken cell types [Horwitz et al., *J. Cell Biol.*, 101, 2134-2144 (1985)], platelets [Sonnenberg et al., *Nature*, 336, 487-489 (1988)], and neuronal cell line PC12 [Tomaselli et al., *J. Cell Biol.*, 105, 2347-2358 (1987); and *J. Cell Biol.*, 107, 1241-1252 (1988)], the laminin receptor was determined to be an integrin. To date, however, the exact sequence of amino acid residues of laminin to which most of these receptors bind is unknown.

Recently, the amino acid sequences of the B1, B2, and A chains of laminin have been determined [Barlow et al., *EMBO J.*, 3, 2355-2362 (1984); Sasaki et al., *Proc. Natl. Acad. Sci. USA*, 84, 935-939 (1987); Sasaki et al., *J. Biol. Chem.*, 263, 16536-16544 (1988); Sasaki and Yamada, *J. Biol. Chem.*, 262, 17111-17117 (1987); Pikkarainen et al., *J. Biol. Chem.*, 262, 10454-10462 (1987); Pikkarainen et al., *J. Biol. Chem.*, 263, 6751-6758 (1988); Hartl et al., *Eur. J. Biochem.*, 173, 629-635 (1988)], allowing peptides to be synthesized from domains of laminin with reported functional activity. Three peptides have been synthesized from the B1 chain of laminin which promote cell adhesion. The first peptide, cys-asp-pro-gly-tyr-iso-gly-ser-arg, located near the intersection of the cross, promotes the adhesion of a variety of cells [Graf et al., *Cell*, 48, 989-996 (1987a); *Biochemistry*, 26, 6896-6900 (1987b)] and is thought to bind a 67 kD protein laminin receptor [Graf et al., supra (1987b); Wewer et al., supra (1986)]. The second, peptide F-9 (arg-tyr-val-val-leu-pro-arg-pro-val-cys-phe-glu-lys-gly-met-asn-tyr-thr-val-arg), also promotes the adhesion of a variety of cells and binds heparin (U.S. Pat. No. 4,870,160). A third peptide from the B1 chain of laminin, termed AC15 [arg-ile-gln-asn-leu-leu-lys-ile-thr-asn-leu-arg-ile-lys-phe-val-lys [Kouzi-Koliakos et al., *J. Biol. Chem.*, 264, 17971-17978 (1989)] also binds heparin, and is derived from the outer globule of a lateral short arm. AC15 promotes the adhesion of murine melanoma and bovine aortic endothelial cells [Koliakos et al., *J. Cell Biol.*, 109, 200a (1989)].

Since the A chain was the last chain of laminin for which the entire amino acid sequence was determined, only a few peptides have been described with functional activity. Synthetic peptide PA 21 (residues #1115-1129; cys-gln-ala-gly-thr-phe-ala-leu-arg-gly-asp-asn-pro-gln-gly), which contains the active sequence RGD, induces the attachment of human endothelial cells through an integrin receptor [Grant et al., *Cell*, 58, 933-943 (1989)]. Peptide PA22-2 (residues #2091-2108; ser-arg-ala-arg-lys-gln-ala-ala-ser-ile-lys-val-ala-val-ser-ala-asp-arg), contains the active sequence ile-lys-val-ala-val [Tashiro et al., *J. Biol. Chem.*, 264, 16174-16182 (1989)] and has a number of biological functions such as promoting neuronal process extension [Tashiro et al., supra (1989); Sephel et al., *Biochem. Biophys. Res. Commun.*, 162, 821-829 (1989)].

The functions that have been described above make laminin an important component of many diverse and clinically important processes such as cell migration, cell adhesion, cell growth, cell differentiation, wound healing, nerve regeneration, tumor cell invasion and metastasis [Liotta, *Am. J. Path.*, 117, 339-348 (1984); McCarthy et al., *Cancer Met. Rev.*, 4, 125-152 (1985)], diabetic microangiopathy, and vascular hypertrophy due to hypertension, atherosclerosis and cornary artery disease, and vessel wall healing after angioplasty. Laminin could also be used in various devices and materials used in humans. In order to better understand the pathophysiology of these processes at the molecular level, it is important to try to assign each of the biological activities that laminin exhibits to a specific subdomain or oligopeptide of laminin. If this can be achieved, potentially important pharmaceuticals based on small peptides producing specific functions of the native, intact molecule, can be synthesized.

Therefore, a need exists to isolate and characterize peptides which are responsible for the wide range of biological activities associated with laminin. Such lower molecular weight oligopeptides would be expected to be more readily obtainable and to exhibit a narrower profile of biological activity than laminin itself, thus increasing their potential usefulness as therapeutic or diagnostic agents.

BRIEF DESCRIPTION OF THE INVENTION

The present invention provides polypeptides which represent fragments of the large globular terminal domain [G domain as denoted by Sasaki et al., supra (1988)] of the A chain of laminin. These polypeptides are at least 5 amino acids in length and can be prepared by conventional solid phase peptide synthesis. The formulas of preferred peptides are:

(R30)
lys—gln—asn—cys—leu—ser—ser—arg—ala—ser—phe—arg—gly—cys—val—arg—asn—leu—arg—leu—ser—arg -continued (R27)
gly—arg—leu—his—phe—met—phe—asp—leu—gly—lys—gly—arg—thr—lys—val—ser—his—pro—

(R33)
gly—thr—lys—asp—phe—leu—ser—iso—glu—leu—val—arg—gly—arg—val—lys—val—met—val—asp—

(R36)
his—ser—iso—ser—leu—val—arg—asn—arg—arg—val—iso—thr—iso—gln (R37)
lys—ala—thr—pro—met—leu—lys—met—arg—thr—ser—phe—his—gly—cys—iso—lys;

and (R38)
lys—glu—gly—tyr—lys—val—arg—leu—asp—leu—asn—iso—thr—leu—glu—phe—arg—thr—thr—ser—lys Polypeptide R30 formally represents isolated laminin residues 3011-3032 from the A chain of laminin; polypeptide R27 formally represents isolated laminin residues 2756-2774 from the A chain of laminin; polypeptide R33 formally represents isolated laminin residues 2333-2352; polypeptide R36 formally represents isolated laminin residues 2567-2581; polypeptide R37 formally represents isolated laminin residues 2615-2631; and polypeptide R38 formally represents isolated laminin residues 2890-2910 from the deduced sequence of the EHS laminin A chain. The single letter amino acid codes for these polypeptides are KQNCLSSRASFRGCVRNLRLSR, GRLHFMFDLGKGRTKVSHP, GTKDFLSIELVRGRVKVMVD, HSISLVRNRRVITIQ, KATPMLKMRTSFHGCIK, and KEGYKVRLDLNITLEFRTTSK, respectively.

These synthetic polypeptides were assayed for bioactivity and found to be potent promoters of heparin binding to synthetic substrates and of cell adhesion including adhesion of: (a) melanoma cells, (b) fibrosarcoma cells, (c) human colon cells, and (d) human renal cells. Therefore, it is believed that these polypeptides, among many other things, may be useful to: (a) assist in nerve regeneration, (b) promote wound healing and implant acceptance, (c) promote cellular attachment and growth on culture substrata, and (d) inhibit the metastasis of malignant cells. Due to the difference in the spectra of biological activities exhibited by the polypeptides described herein, mixtures of these peptides are within the scope of the invention.

Furthermore, since it is expected that further digestion/hydrolysis of polypeptides from the G domain of the A chain of laminin in vitro or in vivo will yield fragments of substantially equivalent bioactivity, such lower molecular weight polypeptides are considered to be within the scope of the present invention. For example, while preferred G domain polypeptides of the A chain of laminin described herein have sequences of at least 15 amino acids, it is to be understood that polypeptides having shorter sequences of amino acids and with functionally active sequences are within the scope of the invention. For example, polypeptides having sequences of fewer than 10 amino acids with functionally active sequences are within the scope of the invention. Further, it is believed that polypeptides having sequences of at least about 5 amino acids with functionally active sequences are within the scope of the invention.

BRIEF DESCRIPTION OF THE DRAWINGS

FIG. 3 reports $^3$H-heparin (approximately 16,000 dpm; homogeneous for size and charge) added to wells adsorbed with increasing concentrations of HPLC-purified peptides R38 (◯) and R35 (△), or BSA (▲) for two hours. Note that these two peptides have the same net charge (+2) and similar hydropathy values (−10.1 and −11.8, respectively). The incubation buffer was 0.02M Tris, pH 6.8 containing 0.05M NaCl and 2 mg/ml ovalbumin. The wash buffer was the same as the incubation buffer with the addition of 0.2% CHAPS. Each value represents the mean of two separate determinations and the S.E. was less than 5% in each case.

FIG. 4 reports results in microtiter wells adsorbed with increasing concentrations of HPLC-purified peptides R38 (◯) and R35 (△), or BSA (▲) and radiolabeled HT-1080 human fibrosarcoma cells that were allowed to adhere for 30 minutes after being released from flasks with EDTA/trypsin. Each value represents the mean of three separate determinations, and the SEM was less than 10% in each case.

FIG. 13 shows human HT-1080 fibrosarcoma cell spreading on a plastic surface coated with BSA (negative control protein).

FIG. 15 reports results in microtiter wells adsorbed with 0.7 μg of laminin to which cells pre-incubated for 30 minutes in increasing concentrations of HPLC-purified peptides R38 (◯) or R35 (△) were added and incubated for 30 minutes. Each value represents the mean of three separate determinations and the SEM was less than 10% in each case.

DETAILED DESCRIPTION OF THE INVENTION

Structure of Laminin and the A Chain

Figure 1:
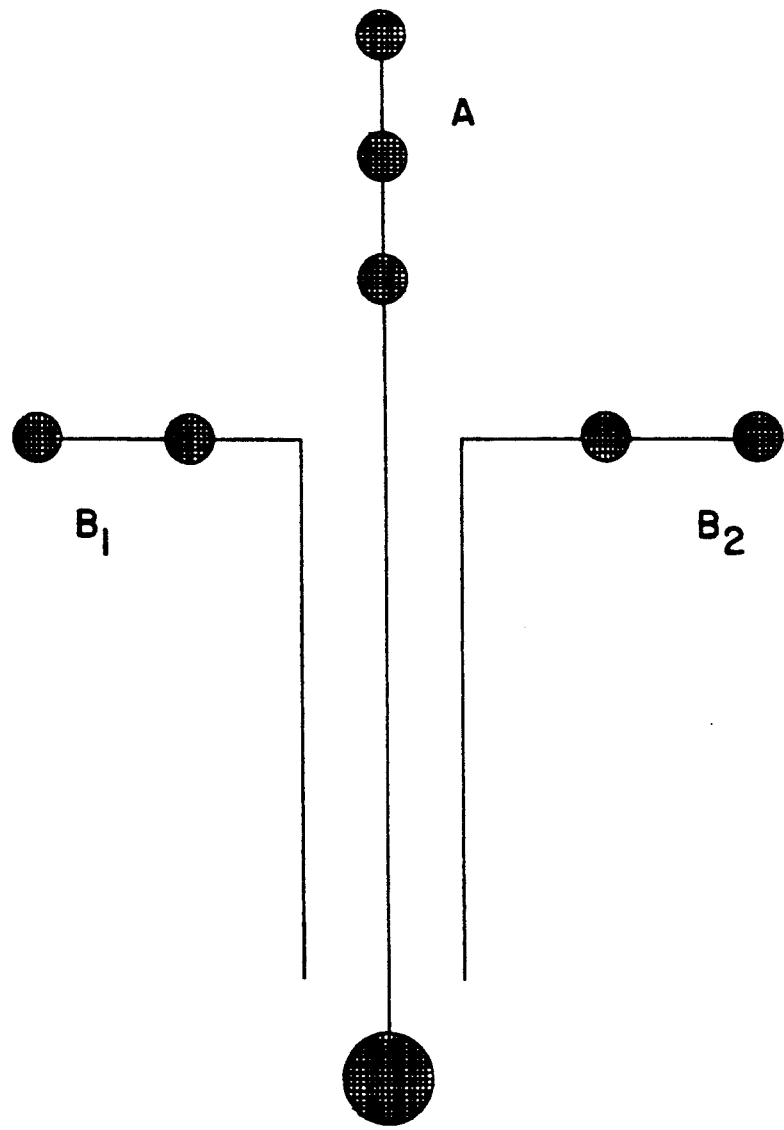
FIG. 1 is a diagrammatic depiction of laminin, indicating the relative location of the A, B1 and B2 chains including globular regions located on each chain.
Figure 2:
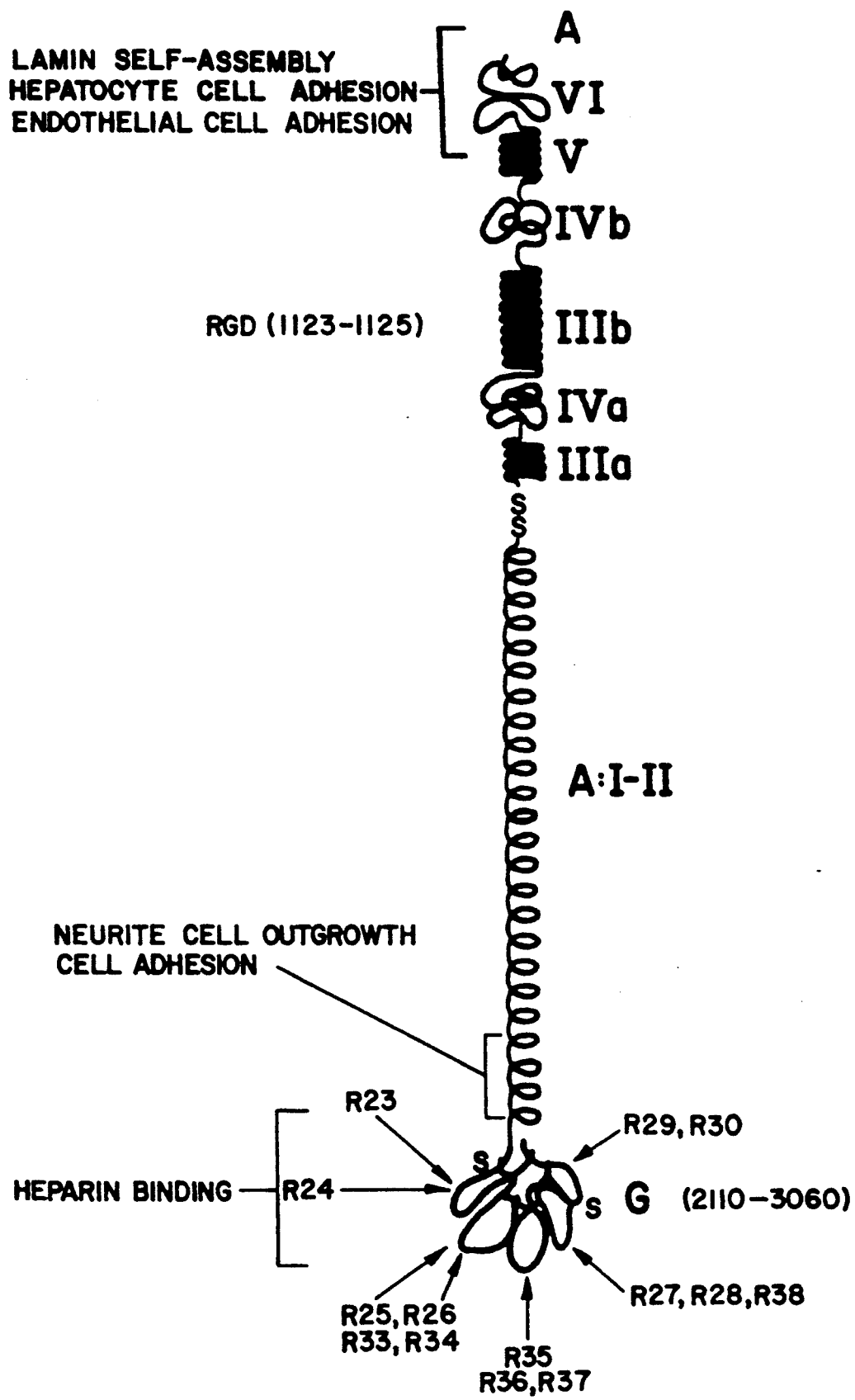
FIG. 2 is a diagrammatic depiction of the A chain of laminin, including the globular G domain. The location of certain synthetic peptides is shown.

Referring to FIG. 1, when examined by the electron microscope utilizing rotary shadowing techniques, the structure of laminin derived from the mouse EHS tumor appears as an asymmetric cross. The three short arms each have multiple globular domains and are 37 nm in length. The long arm exhibits one large terminal globular domain and is 77 nm in length [Engel et al., supra (1981)]. Laminin likely is one of a multigene family of related molecules [(Ohno et al., supra (1986); Hunter et al., supra (1989)]. As seen in FIG. 1, the three chains are associated via disulfide bonds and other chemical bonds. The amino acid sequences of all three polypeptide chains of laminin have now been deduced by sequencing isolated clones having specific laminin genes [Sasaki et al., supra (1988); Sasaki and Yamada, supra (1987); Sasaki et al., J. Biol. Chem., supra (1988)]. Taken together, the three chains are composed of a total of 6,456 amino acids. A diagrammatic of the A chain is shown in FIG. 2.

Binding sites for heparin are of special interest since heparin-like macromolecules such as heparan sulfate proteoglycans are present in basement membranes and cell surfaces and therefore their association with laminin may affect basement membrane structure and diverse cellular functions. Also, many growth factors bind heparin and the association of laminin to heparin-like molecules and growth factors may be a way of controlling a cell's microenvironment and growth potential. As indicated previously, it is known that a heparin binding site exists on the A chain, in the globule of the long arm of laminin [Ott et al., supra (1982); Skubitz et al., supra (1988)]; the exact amino acid sequence is not known and therefore no related oligopeptide has been identified.

According to the present invention, we have investigated the G domain of the A chain of laminin and synthesized a number of peptide fragments with cell attachment promoting activity. We synthesized 14 peptides, each of ~20 amino acid residues in length, from the published amino acid sequence of the terminal globular domain of the A chain of laminin [Sasaki et al., supra (1988)]. The polypeptides synthesized and their properties are set forth in Tables I and II, respectively. Peptides R27, R30, R33, R36, R37, and R38 are preferred embodiments of the present invention.

TABLE I

| Laminin A Chain Peptides Synthesized | | | | |
|---|---|---|---|---|
| Peptide | Sequence* | Sequence Numbers* | Net Charge | Hydropathy Index § |
| R23 | DFLAVEMRRGKVAFLWD | 2149–2165 | 0 | −5.0 |
| R24 | QIKKSPAVKVTHFKGCMG | 2240–2257 | +5 | −4.4 |

TABLE I-continued

Laminin A Chain Peptides Synthesized

| Peptide | Sequence* | Sequence Numbers* | Net Charge | Hydropathy Index § |
|---|---|---|---|---|
| R25 | TDRRYNNGTWYKIAFQRNRKQ | 2362–2382 | +5 | −35.1 |
| R26 | KNLEISRSTFDLLRNSYGVRK | 2443–2463 | +3 | −8.6 |
| R27 | GRLHFMFDLGKGRTKVSHP | 2756–2774 | +5 | −8.2 |
| R28 | DGKWHTVKTEYIKRKAF | 2779–2795 | +4 | −17.8 |
| R29 | RAARALCDGKWHTLQAHKSKHR | 2952–2973 | +8 | −20.2 |
| R30 | KQNCLSSRASFRGCVRNLRLSR | 3011–3032 | +6 | −8.9 |
| R33 | GTKDFLSIELVRGRVKVMVD | 2333–2352 | +1 | +5.0 |
| R34 | HSKAVRKGVSSRSYVGC | 2425–2441 | +5 | −6.5 |
| R35 | TSLRKALLHAPTGSYSDGQ | 2547–2565 | +2 | −11.8 |
| R36 | HSISLVRNRRVITIQ | 2567–2581 | +4 | −0.4 |
| R37 | KATPMLKMRTSFHGCIK | 2615–2631 | +5 | −5.1 |
| R38 | KEGYKVRLDLNITLEFRTTSK | 2890–2910 | +2 | −10.1 |

*Based on Sasaki et al. 1988. [G = Glycine; A = Alanine; V = Valine; L = Leucine; I = Isoleucine; F = Phenylalanine; Y = Tyrosine; W = Tryptophan; M = Methionine; C = Cysteine; S = Serine; T = Threonine; H = Histidine; K = Lysine; R = Arginine; D = Aspartate; E = Glutamate; N = Asparagine; Q = Glutamine; P = Proline.]

Calculated by assuming a +1 net charge for lysine (K) and arginine (R) residues and a −1 net charge for glutamic acid (E) and aspartic acid (D) at neutral pH. Histidine is assumed to be uncharged at this pH.

§ Calculated by the method of Kyte and Doolittle (1982). According the this method, more hydrophobic peptides correspond to the more positive numerical values. We constructed hydropathy plots for the entire A chain of laminin using a Sun Computer and an intelliGenetics (Mountain View, CA) program with a span setting of 6-7 amino acids.

Synthesis of the Polypeptide

The peptides listed in Table I (designated R-series), were derived from the large terminal globular domain, G (residues #2110-3060) of the A chain of EHS laminin. They were synthesized, then HPLC-purified as previously described by Charonis et al., J. Cell Biol., 107, 1253-1260 (1988). Purity was checked by HPLC and amino acid analysis. Specifically, the polypeptides of the invention were synthesized using the Merrifield solid phase method. This is the method most commonly used for peptide synthesis, and it is extensively described by J. M. Stewart and J. D. Young in Solid Phase Peptide Synthesis, Pierce Chemical Company, pub., Rockford, Ill. (2d ed., 1984), the disclosure of which is incorporated by reference herein.

The Merrifield system of peptide synthesis uses a 1% crosslinked polystyrene resin functionalized with benzyl chloride groups. The halogens, when reacted with the salt of a protected amino acid will form an ester, linking it covalently to the resin. The benzyloxy-carbonyl (BOC) group is used to protect the free amino group of the amino acid. This protecting group is removed with 25% trifluoroacetic acid (TFA) in dichloromethane (DCM). The newly exposed amino group is converted to the free base by 10% triethylamine (TEA) in DCM. The next BOC-protected amino acid is then coupled to the free amino of the previous amino acid by the use of dicyclohexylcarbodiimide (DCC). Side chain functional groups of the amino acids are protected during synthesis by TFA stable benzyl derivatives. All of these repetitive reactions can be automated, and the peptides of the present invention were synthesized by hand or at the University of Minnesota Microchemical facility by the use of a Beckman System 990 Peptide synthesizer.

Following synthesis of a blocked polypeptide on the resin, the polypeptide resin is treated with anhydrous hydrofluoric acid (HF) to cleave the benzyl ester linkage to the resin and thus to release the free polypeptide. The benzyl-derived side chain protecting groups are also removed by the HF treatment. The polypeptide is then extracted from the resin, using 1.0M acetic acid, followed by lyophilization of the extract. Lyophilized crude polypeptides are purified by preparative high performance liquid chromatography (HPLC) by reverse phase technique on a C-18 column. A typical elution gradient is 0% to 60% acetonitrile with 0.1% TFA in $H_2O$. Absorbance of the eluant is monitored at 220 nm, and fractions are collected and lyophilized.

Characterization of the purified polypeptide is by amino acid analysis. The polypeptides are first hydrolyzed anaerobically for 24 hours at 110° C. in 6M HCl (constant boiling) or in 4N methanesulfonic acid, when cysteine or tryptophan are present. The hydrolyzed amino acids are separated by ion exchange chromatography using a Beckman System 6300 amino acid analyzer, using citrate buffers supplied by Beckman. Quantitation is by absorbance at 440 and 570 nm, and comparison with standard curves. The polypeptides may be further characterized by amino acid sequence determination. This approach is especially useful for longer polypeptides, where amino acid composition data are inherently less informative. Sequence determination is carried out by sequential Edman degradation from the amino terminus, automated on a Model 470A gas-phase sequenator (Applied Biosystems, Inc.), by the methodology of R. M. Hewick et al., J. Biol. Chem., 256, 7990 (1981).

Protein Isolation

Laminin was isolated from the EHS tumor as described by Palm and Furcht, J. Cell Biol., 96, 1218-1226 (1983) with minor modifications. Specifically, tumor tissue was homogenized in 3.4M NaCl, 0.01M phosphate buffer, pH 7.4, with 50 μg/ml of the protease inhibitors PMSF (Sigma Chemical Co., St. Louis, Mo.) and p-hydroxymercuribenzoate (Sigma Chemical Co.), washed twice with the same buffer, then extracted overnight with 0.5M NaCl, 0.01M phosphate, pH 7.4, and 50 μg/ml of the protease inhibitors. The salt concentration was raised to 1.7M followed by stirring overnight at 4° C., then spun at 15,000 rpm for 15 minutes. Laminin was precipitated from the supernatant overnight at 4° C. with 30% saturation ammonium sulfate. The precipitate was resuspended in 0.5M NaCl, 0.01M phosphate, pH 7.4, and dialyzed against the same buffer. Aggregates were removed by ultracentrifugation at 40,000 g for 1 hour at 4° C. Laminin was isolated from the supernatant by gel filtration chromatography on Sephacryl S-300

(Pharmacia Fine Chemicals, Piscataway, N.J.) (2.6×100 cm column) in the 0.5M NaCl buffer, where it eluted just after the void volume. The laminin solution was concentrated by evaporation while in a dialysis bag, dialyzed against PBS and stored at −70° C. Type IV collagen was isolated from the EHS tumor [Herbst et al., *J. Cell Biol.*, 106, 1365-1373 (1988)] and fibronectin was isolated from human plasma as described previously by McCarthy et al., *J. Cell Biol.*, 102, 179-188 (1986). The purity of all three proteins was verified by SDS-PAGE and ELISA. BSA (grade V, fatty acid free) was purchased from Sigma Chemical Co.

The invention will be further described by reference to the following detailed examples.

EXAMPLE 1

Heparin Binding to Plastic Plates Coated with Peptides

The binding of $^3$H-heparin to laminin A chain peptides was measured in a direct solid phase binding assay as described below, whereby various amounts of the peptides were adsorbed to plates and $^3$H-heparin was added to each well. More specifically, the binding of $^3$H-heparin (0.3 mCi/mg; Du Pont - New England Nuclear Research Products, Wilmington, Del.) to laminin, synthetic peptides, and bovine serum albumin (BSA) (fatty acid free, fraction V, ICN Immunobiologicals) was quantititated by a solid-phase RLBA in 96-well polystyrene Immulon 1 plates (Dynatech Laboratories, Inc., Alexandria, Va.) as described by Skubitz et al., supra (1988). Specifically, 50 microliters of the various proteins at various concentrations (0.2 µg/well-5.0 µg/well) in PBS containing 0.02% NaN$_3$ was added to each well and dried overnight at 29° C. The next day, 200 µl of 2 mg/ml BSA in PBS was added to each well, followed by a 2 hour incubation at 37° C. After removal of this buffer, 50 µl of $^3$H-heparin (200,000 dpm) was added in RLBA buffer (20 mM Tris, pH 6.8 containing 50 mM NaCl and 2 mg/ml ovalbumin) and the wells were incubated at 37° C. for 2 hours. Unbound $^3$H-heparin was removed by washing three times with wash buffer (RLBA buffer containing 0.1% CHAPS). Tritiated heparin was solubilized by incubation with 200 µl of 0.05N NaOH and 1% SDS for 30 minutes at 60° C. and quantitated in a Beckman LS-3801 scintillation counter.

Figure 3:
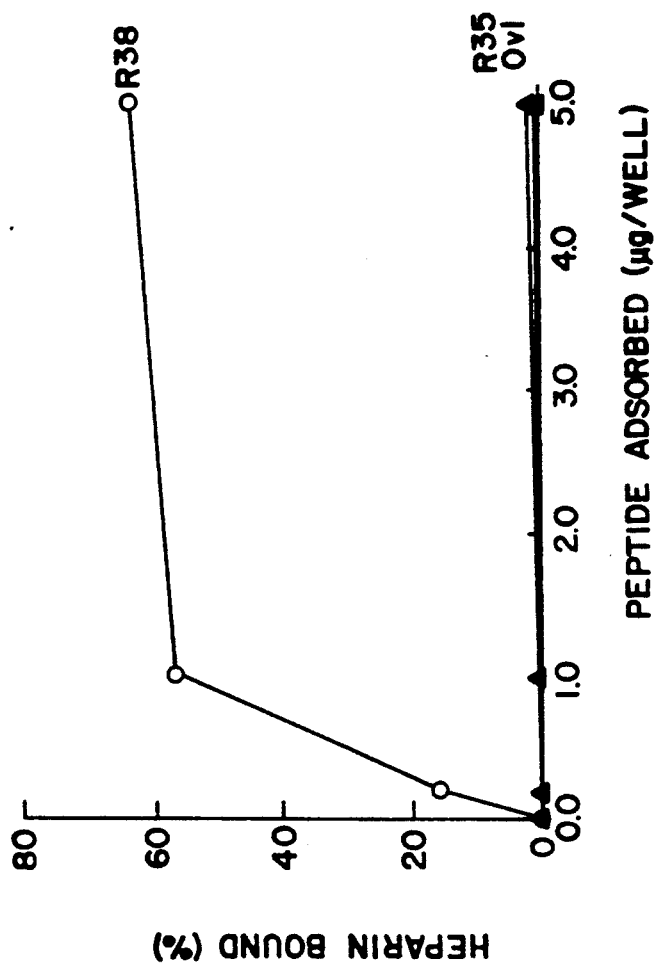
FIG. 3 is a graph showing binding of $^3$H-heparin to laminin A chain peptides.

The amount of $^3$H-heparin which bound to 2 µg of each of the peptides is summarized in Table II. The results show that the peptides are ranked in order of decreasing net charge, along with their hydropathy index. The peptides can be categorized into one of three groups based on their heparin binding activity: (1) very good heparin binding (R30, R33, R37, and R38); (2) moderate heparin binding (R23, R27, R29, and R36); and (3) poor heparin binding (R24, R25, R26, R28, R34, and R35). Interestingly, no correlation was observed between the net charge, hydropathy index, or heparin binding activity of the peptides. For example, peptides R38 and R35 both have the same net charge of +2, and very similar hydropathy values (−10.1 and −11.8, respectively); however, only peptide R38 binds $^3$H-heparin. Furthermore, the binding of $^3$H-heparin to peptide R38 (and the other heparin binding peptides, not shown) occurred in a concentration-dependent manner (FIG. 3).

TABLE II $^3$H-Heparin Binding to Laminin A Chain Peptides is Independent of Net Charge and Hydropathy Index

| Peptide | Net Charge | Hydropathy Index | Heparin Binding* |
|---------|------------|------------------|------------------|
| R29 | +8 | −20.2 | ** |
| R30 | +6 | −8.9 | **** |
| R24 | +5 | −4.4 | — |
| R25 | +5 | −35.1 | * |
| R34 | +5 | −6.5 | * |
| R27 | +5 | −8.2 | *** |
| R37 | +5 | −5.1 | **** |
| R28 | +4 | −17.8 | — |
| R36 | +4 | −0.4 | *** |
| R26 | +3 | −8.6 | — |
| R35 | +2 | −11.8 | — |
| R38 | +2 | −10.1 | **** |
| R33 | +1 | +5.0 | **** |
| R23 | 0 | −5.0 | ** |

*One microgram of each peptide was adsorbed to the plates and 200,000 dpm of $^3$H-heparin in 20 mM Tris, pH 6.8, 50 mM NaCl, 2 mg/ml ovalbumin was added. The bound $^3$H-heparin is expressed as a percent of the input $^3$H-heparin: 0–1.9% (−); 2.0–3.9% (*); 4.0–5.9% (); 6.0–10.0% (*); >10% [****]. Since saturating amounts of $^3$H-heparin were added, the percent of $^3$H-heparin bound is relatively low.

The above experimental procedure was repeated to determine the percentage of $^3$H-heparin that would adhere to 2 µg/well of each polypeptide after a two-hour incubation in increasing concentrations of salt (NaCl). The results are reported below in Table III.

TABLE III

Laminin A Chain Peptides Bind Heparin in Increasing Salt Concentrations

| Peptide | 0.05M NaCl | 0.15M NaCl | 0.5M NaCl | 1.0M NaCl |
|---------|-----------|-----------|-----------|-----------|
| R24 | — | — | — | — |
| R25 | ** | ** | * | — |
| R26 | — | — | — | — |
| R27 | *** | *** | ** | — |
| R28 | — | — | — | — |
| R30 | **** | **** | *** | * |
| R33 | **** | **** | ** | — |
| R34 | * | * | — | — |
| R35 | — | — | — | — |
| R36 | *** | *** | *** | * |
| R37 | **** | **** | *** | * |
| R38 | **** | **** | *** | * |
| Ovalbumin | — | — | — | — |

Two micrograms of each peptide was adsorbed to the plates and a saturating amount of $^3$H-heparin (200,000 dpm) was added in 0.02M Tris buffer, pH 6.8 containing various concentrations of NaCl. The plates were incubated for 2 hr at 37° C., washed, and the amount of $^3$H-heparin bound was quantitated. The bound $^3$H-heparin is expressed as a percent of the input $^3$H-heparin: 0–1.9% (−); 2.0–3.9% (*); 4.0–5.9% (); 6.0–10.0% (*); >10% (****). Since saturating amounts of $^3$H-heparin were added, the percent of $^3$H-heparin bound is relatively low; however, on a molar basis this binding is quite significant.

Preferred peptides exhibited high affinity of binding, even in the presence of a high salt concentration (1.0M NaCl).

EXAMPLE 2

Cell Adhesion Assays

Cells

The murine melanoma K-1735-C10 (low metastatic) and K-1735-M4 (high metastatic) cell lines, murine UV-2237-MM fibrosarcoma cell line, human renal carcinoma SN12 C (low metastatic) and SN12 PM-6 (high metastatic) cell lines, and human colon carcinoma KM12 C (low metastatic) and KM12 SM (high metastatic) cell lines were originally provided by Dr. I. J. Fidler (M.D., Anderson Hospital, University of Texas Health Sciences Center, Houston, Tex.). The human fibrosarcoma HT-1080 cell line was obtained from the ATCC. The MM fibrosarcoma cell line was maintained in DME (GIBCO Laboratories, Grand Island, N.Y.) containing 10% FBS, the murine melanomas were maintained in DMEM containing 10% calf serum, the human fibrosarcoma cells were maintained in EMEM containing 10% heat inactivated FBS, and the human renal and colon carcinoma cells were grown in EME containing 10% FBS, vitamins, and 1 mM sodium pyruvate. Cells were passaged for 4 to 5 weeks and then replaced from frozen stocks of early passage cells to minimize phenotypic drift. Cells were maintained at 37° C. in a humidified incubator containing 5% $CO_2$.

tides that were very good at binding heparin (i.e., R30, R33, R37, and R38) were also capable of promoting the adhesion of all eight cell lines. Further, the peptides which bound heparin moderately (i.e., R23, R27, R29, and R36) also promoted cell adhesion; whereas those peptides which bound heparin poorly or did not bind heparin at all (i.e., R24, R25, R26, R28, R34, and R35) were, in some cases, less active or inactive at promoting cell adhesion. Many of the peptides that were very good at binding heparin and cells were also capable of inhibiting the adhesion of various cells to surfaces coated with laminin (see below).

TABLE IV

Direct Cell Adhesion to Surfaces Coated with 1 μg of Laminin Synthetic Peptides

| | | | Laminin A Chain Synthetic Peptides | | | | | | | | | | | | | |
|---|---|---|---|---|---|---|---|---|---|---|---|---|---|---|---|---|
| | Proteins | | Very Good Heparin Binding | | | | Moderate Heparin Binding | | | | For Heparin Binding | | | | | |
| Cell Line | LMN | BSA | R30 | R33 | R37 | R38 | R23 | R27 | R29 | R36 | R24 | R25 | R26 | R28 | R34 | R35 |
| | | | | | | Percentage of Cells Adhered to Surface | | | | | | | | | | |
| murine melanoma (M4) | 13 | 3 | 25 | 28 | 34 | 39 | 10 | 34 | 17 | 21 | 36 | ND | 25 | 27 | 26 | 2 |
| murine melanoma (C10) | 58 | 1 | 82 | 39 | 44 | 98 | 76 | 78 | 38 | 40 | ND | ND | ND | ND | 42 | ND |
| murine fibrosarcoma (MM) | 53 | 1 | 56 | 53 | 50 | 74 | 67 | 53 | 44 | 47 | ND | 44 | ND | ND | 47 | ND |
| human colon (KM12 SM) | ND | ND | 69 | 53 | 41 | 54 | ND | 72 | 32 | 61 | ND | ND | ND | ND | 9 | ND |
| human colon (KM12 C) | 11 | 1 | 48 | 40 | 32 | 70 | ND | 39 | 33 | 38 | ND | ND | ND | ND | 34 | ND |
| human renal (SN12 PM6) | 36 | 1 | 67 | 86 | 65 | 82 | ND | 89 | 58 | 77 | ND | ND | ND | ND | 64 | ND |
| human renal (SN12C) | 28 | 11 | 84 | 89 | 79 | 95 | ND | 75 | 30 | 78 | ND | ND | ND | ND | 63 | ND |
| human fibrosarcoma (HT1080) | 41 | 3 | 92 | 91 | 92 | 90 | ND | 95 | ND | 62 | 64 | 85 | 45 | 36 | 93 | 2 |

Assay Procedure and Results

The direct adhesion of cells to protein or peptide coated surfaces was performed as described in Skubitz et al., *Exp. Cell Res.*, 173, 349-360 (1987) and Charonis et al., supra (1988). Briefly, radiolabeled cells were added to 96-well microtiter plates coated with various concentrations of synthetic peptides, laminin, or BSA (0.02 μg/well-50 μg/well from 50 μl solutions) for various lengths of time. After the incubation period, loosely or nonadherent cells were removed by washing the wells three times. Adherent cells were solubilized and quantitated in a scintillation counter. More specifically, cultures of cells which were 60-80% confluent were metabolically labeled for 24 hours with the addition of 3 μCi/ml of $^3$H-td (tritiated thymidine). On the day of the assay, the cells were harvested by trypsinization, the trypsin was inhibited by the addition of serum, and the cells were washed free of this mixture and resuspended in DMEM buffered with HEPES at pH 7.2. The adhesion medium also contained 2 mg/ml BSA. The cells were adjusted to a concentration of $3-4 \times 10^4$/ml, and 100 μl of this cell suspension was added to the wells. The assay mixture was then incubated at 37° C. for 120 minutes. At the end of the incubation, the wells were washed with warm DMEM/Hepes containing 2 mg/ml BSA, and the adherent population was solubilized with 0.5N NaOH contained 1% SDS. The solubilized cells were then quantitated using a liquid scintillation counter.

Instead of attempting to characterize the cell binding activity of all 14 of the synthetic peptides, a number of peptides from each of the three heparin binding categories of peptides were evaluated. Microtiter wells were adsorbed with the peptides, laminin, or BSA and a variety of tumor cell lines were tested for the ability to adhere to the ligands. The eight different cell lines selected for this study were of murine or human origin and, in most cases, of either high or low metastatic capacity. As reported in Table IV, all of the four pep- Based on their ability to promote heparin binding and cell adhesion, the peptides were observed to fall into three categories: Group I peptides bind heparin and promote cell adhesion; Group II peptides do not bind heparin, but do promote cell adhesion; and Group III peptides bind neither heparin nor cells.

Figure 4:
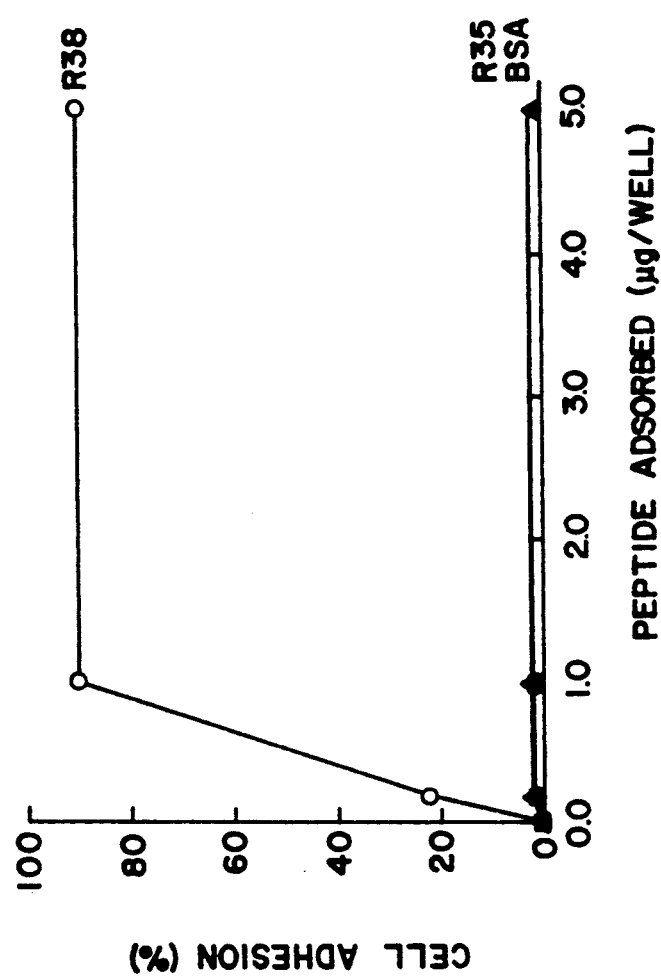
FIG. 4 shows adhesion of HT-1080 human fibrosarcoma cells to laminin A chain peptides.

A representative example of the adhesion of cells to synthetic peptides is shown in FIG. 4. In this case, increasing concentrations of two synthetic peptides of similar net charge, R38, which binds $^3$H-heparin, and R35, which does not bind $^3$H-heparin, were adsorbed to microtiter wells. Radiolabeled HT-1080 human fibrosarcoma cells were incubated in the wells for 30 minutes and the adhesion of cells was quantitated. Cells adhered to peptide R38 in a concentration-dependent, saturable manner with maximal cell adhesion of approximately 90% occurring when wells were adsorbed with 1 μg of peptide R38. In contrast, no cell adhesion was observed in wells adsorbed with peptide R35, even at concentrations as high as 5 μg/well. Similar patterns of concentration-dependence and saturability were observed for the other synthetic peptides which promoted cell adhesion (not shown). No cell adhesion was observed in wells adsorbed with BSA or peptide F-11 [Charonis et al., supra (1988)].

EXAMPLE 3

Inhibition of Cell Adhesion to Surfaces Coated with Laminin

Inhibition of cell adhesion with synthetic peptides was performed using assays similar to those described by Skubitz et al., supra (1987). Briefly, radiolabeled cells at $5 \times 10^4$/ml were incubated for 30 minutes with various concentrations of synthetic peptides (1.0 μg/ml-200 μg/ml) in DME/Hepes containing 2 mg/ml BSA. One hundred microliters of the cell suspension was then added to wells precoated with 1.5 μg of laminin, 1.0 μg of type IV collagen, or 1.0 μg of fibronectin. The cells were incubated for 30 minutes at 37° C., then the wells were washed and adherent cells were quantitated as previously described [Skubitz et al., supra (1987)]. Cell viability after a one hour incubation in the presence of the "inhibitors" was assessed by trypan blue dye exclusion. In all cases, the cells were >95% viable, and no toxicity of the peptides was observed at the indicated concentrations tested. Inhibition of cell adhesion by 10 µg/ml of the laminin A chain peptides is reported in Table V.

were measured per well; each experiment was done in quadruplicate and repeated three times. The quantitation of spreading for four different cell lines is shown in Table VI. In all cases, the cells spread on the peptides to occupy an area about 60% of that seen on laminin-coated surfaces.

As seen in FIGS. 5-14, human HT-1080 fibrosarcoma cell spreading on laminin synthetic peptides from the A chain is shown. The spreading was quantitated (Table

TABLE V

Inhibition of Cell Adhesion to Surfaces Coated with 1.5 µg of Laminin by Laminin A Chain Peptides

| | Laminin A Chain Synthetic Peptides | | | | | | | | | | | | |
|---|---|---|---|---|---|---|---|---|---|---|---|---|---|
| | Very Good Heparin Binding | | | | Moderate Heparin Binding | | | | Poor Heparin Binding | | | | |
| Cell Line | R30 | R33 | R37 | R38 | R23 | R27 | R29 | R36 | R24 | R26 | R28 | R34 | R35 |
| | Percentage Inhibition of Laminin-Mediated Cell Adhesion* | | | | | | | | | | | | |
| murine melanoma (M4) | 38 | ND | 81 | 59 | 86 | 82 | ND | ND | ND | ND | ND | ND | ND |
| murine melanoma (C10) | 22 | 0 | 0 | 41 | 21 | 7 | 79 | 94 | ND | ND | ND | 0 | ND |
| murine fibrosarcoma (MM) | 25 | 21 | 49 | 56 | 40 | 56 | 0 | 0 | ND | ND | ND | 0 | ND |
| human colon (KM12 C) | 59 | 76 | 62 | 64 | ND | 72 | ND | 0 | ND | ND | ND | 0 | ND |
| human renal (SN12 PM6) | 44 | 79 | 48 | 53 | ND | 76 | 4 | 42 | ND | ND | ND | 0 | ND |
| human renal (SN12C) | 0 | 7 | 52 | 4 | ND | 37 | 0 | 0 | ND | ND | ND | 0 | ND |
| human fibrosarcoma (HT1080) | 51 | 51 | 47 | 28 | ND | 84 | ND | 20 | 0 | 32 | 4 | 0 | 0 |

*Exogenous soluble peptides were incubated with all cell lines at 10 µg/ml, except for the HT1080 cells which were incubated with the peptides at 20 µg/ml.

EXAMPLE 4

Cell Spreading Assay

Spreading of the adherent cells was evaluated by performing adhesion assays similar to those described above. Twenty-four well tissue culture plates (Becton Dickinson and Co., Lincoln Park, N.J.) were coated with 300 µl of laminin, synthetic peptides, or BSA at 100 µg/ml, then blocked with 2 mg/ml BSA in PBS. Three hundred microliters of a cell suspension at $5 \times 10^4$ cells/ml was added to each well, and after a 2½ hour incubation, nonadherent cells were aspirated out of the wells. Adherent cells were fixed with 2% glutaraldehyde in PBS at 23° C. for one hour. The glutaraldehyde was then removed and the cells were stained by two different techniques. For photographic purposes, the cells were stained with Diff-Quik Solution I (American Scientific Products, McGaw Park, Ill.) for 10 minutes at 23° C. Solution I was removed, then Diff-Quik Solution II was added and the cells were stained for another 10 minutes at 23° C. Wells were washed with PBS, then representative cells were photographed with a Nikon DIAPHOT inverted phase microscope using Panatomic X Film ASA32 (Eastman Kodak, Rochester, N.Y.). Adherent cells to be quantitated for spreading were stained overnight at 23° C. with 500 µl of a solution containing 0.12% (w/v) Coomassie Brilliant Blue R (Sigma Chemical Co.), 5% (v/v) acetic acid, and 50% (v/v) ethanol. Wells were washed three times with 500 µl of PBS and cell spreading was then quantitated by measuring the average surface area occupied by a cell using an Opti-Max Image Analyzer. Thirty cells VII) for each of the peptides, and the 5 peptides of most interest to us are those which promoted the most cell spreading (i.e., R27, R30, R33, R36, R37, and R38).

TABLE VI

Quantitation of Cell Spreading on Surfaces Coated with Laminin A Chain Peptides

| | Protein | | Laminin A Chain Peptides | | |
|---|---|---|---|---|---|
| | LMN | BSA | R30 | R33 | R27 |
| Cell Line | Surface Area Occupied by a Cell (µm²) | | | | |
| murine fibrosarcoma (MM) | 443 ± 32 | 74 ± 11 | 291 ± 21 | 286 ± 22 | N.D. |
| human renal (SN12 PM6) | 550 ± 29 | 75 ± 8 | 311 ± 19 | 287 ± 17 | N.D. |
| human renal (SN12C) | 520 ± 14 | 75 ± 2 | 292 ± 22 | 288 ± 21 | 312 ± 18 |
| human fibrosarcoma (HT1080) | 610 ± 62 | 63 ± 4 | 392 ± 27 | 409 ± 39 | 412 ± 31 |

TABLE VII

Quantitation of HT-1080 Human Fibrosarcoma Cell Spreading on Surfaces Coated with Laminin A Chain Peptides

| Laminin A Chain Peptide | Surface Area Occuppied by a Cell (um2) |
|---|---|
| R24 | 381 +/− 35 |
| R25 | 338 +/− 30 |
| R26 | 360 +/− 27 |
| R27 | 412 +/− 31 |
| R28 | 372 +/− 33 |
| R30 | 392 +/− 27 |
| R33 | 409 +/− 39 |
| R34 | 302 +/− 41 |
| R35 | 59 +/− 4 |
| R36 | 342 +/− 28 |
| R37 | 396 +/− 32 |
| R38 | 388 +/− 29 |
| Laminin | 610 +/− 62 |
| BSA | 63 +/− 4 |

Figure 5:
FIG. 5 shows human HT-1080 fibrosarcoma cell spreading on a plastic surface coated with laminin.
Figure 6:
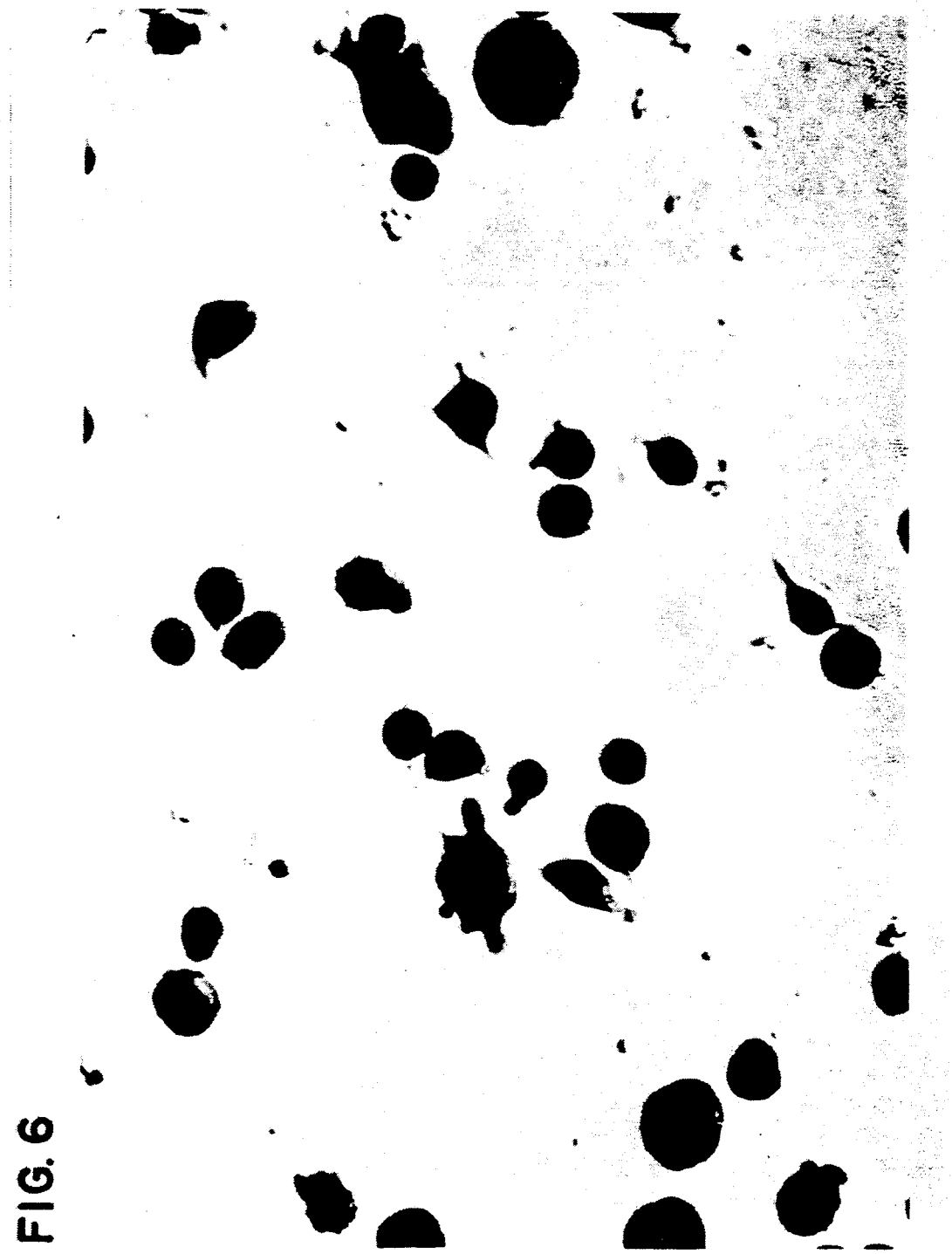
FIG. 6 shows human HT-1080 fibrosarcoma cell spreading on a plastic surface coated with synthetic peptide R22 derived from the A chain of laminin.
Figure 7:
FIG. 7 shows human HT-1080 fibrosarcoma cell spreading on a plastic surface coated with synthetic peptide R25 derived from the A chain of laminin.
Figure 8:
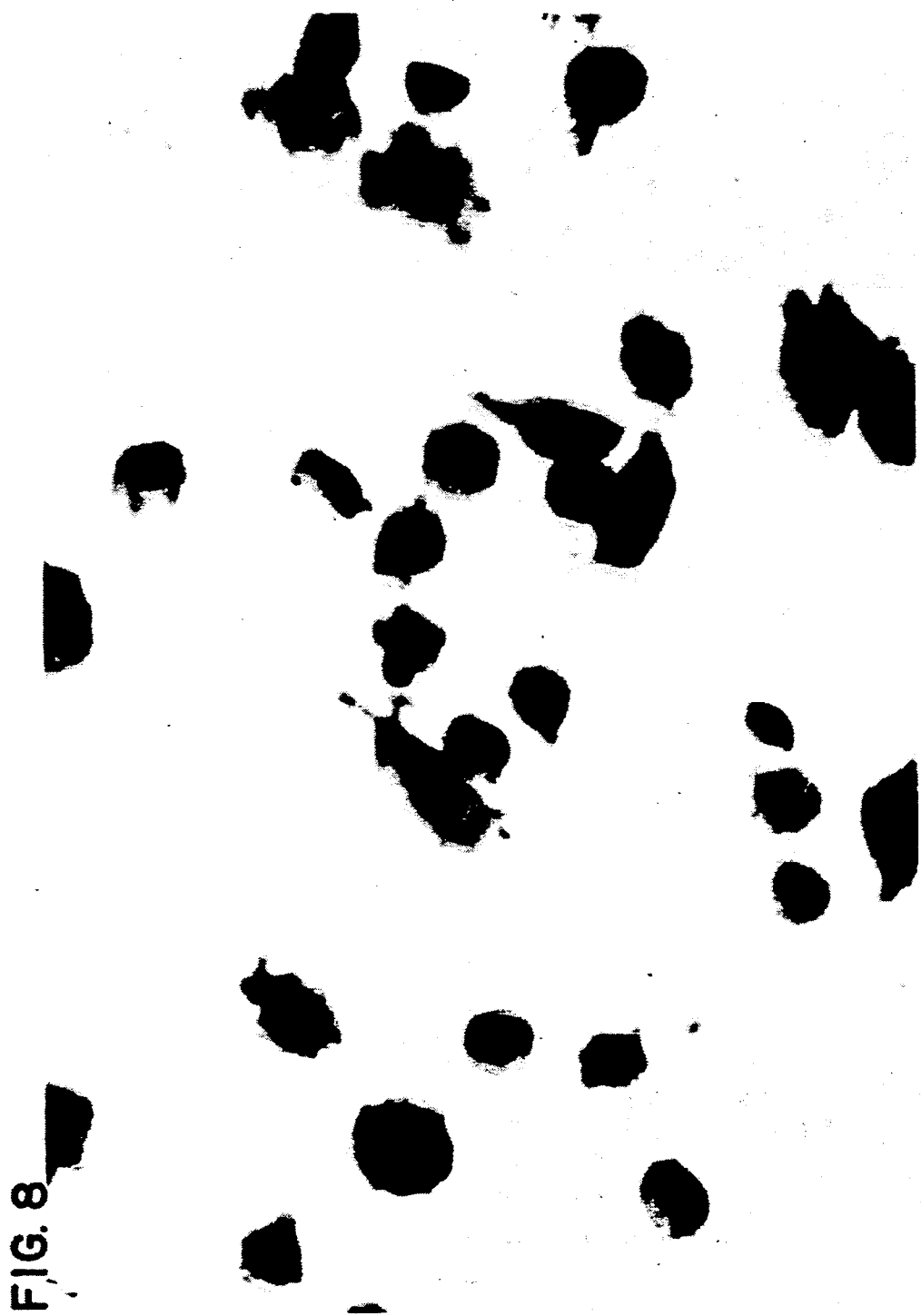
FIG. 8 shows human HT-1080 fibrosarcoma cell spreading on a plastic surface coated with synthetic peptide R27 derived from the A chain of laminin.
Figure 9:
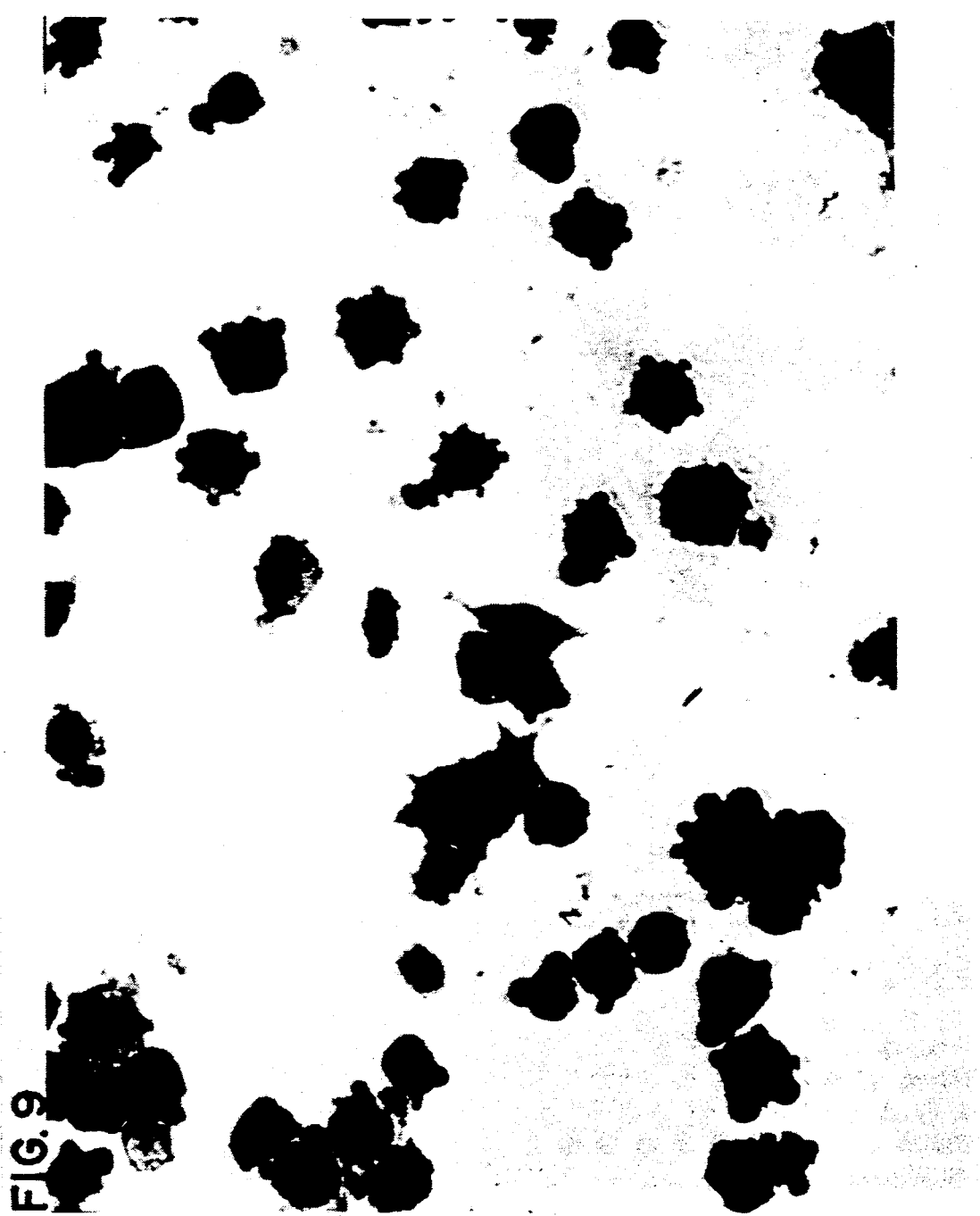
FIG. 9 shows human HT-1080 fibrosarcoma cell spreading on a plastic surface coated with synthetic peptide R30 derived from the A chain of laminin.
Figure 10:
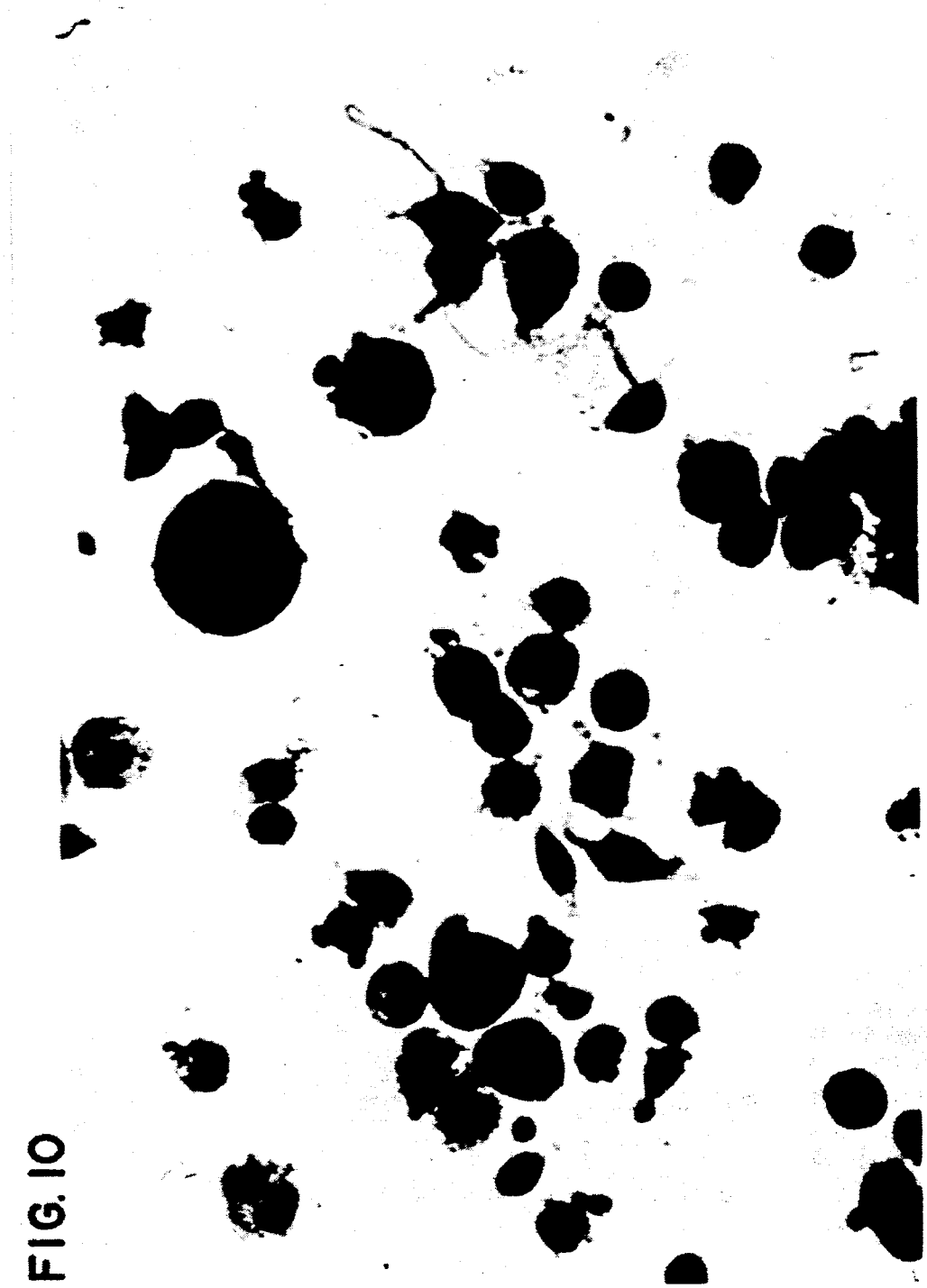
FIG. 10 shows human HT-1080 fibrosarcoma cell spreading on a plastic surface coated with synthetic peptide R33 derived from the A chain of laminin.
Figure 11:
FIG. 11 shows human HT-1080 fibrosarcoma cell spreading on a plastic surface coated with synthetic peptide R37 derived from the A chain of laminin.
Figure 12:
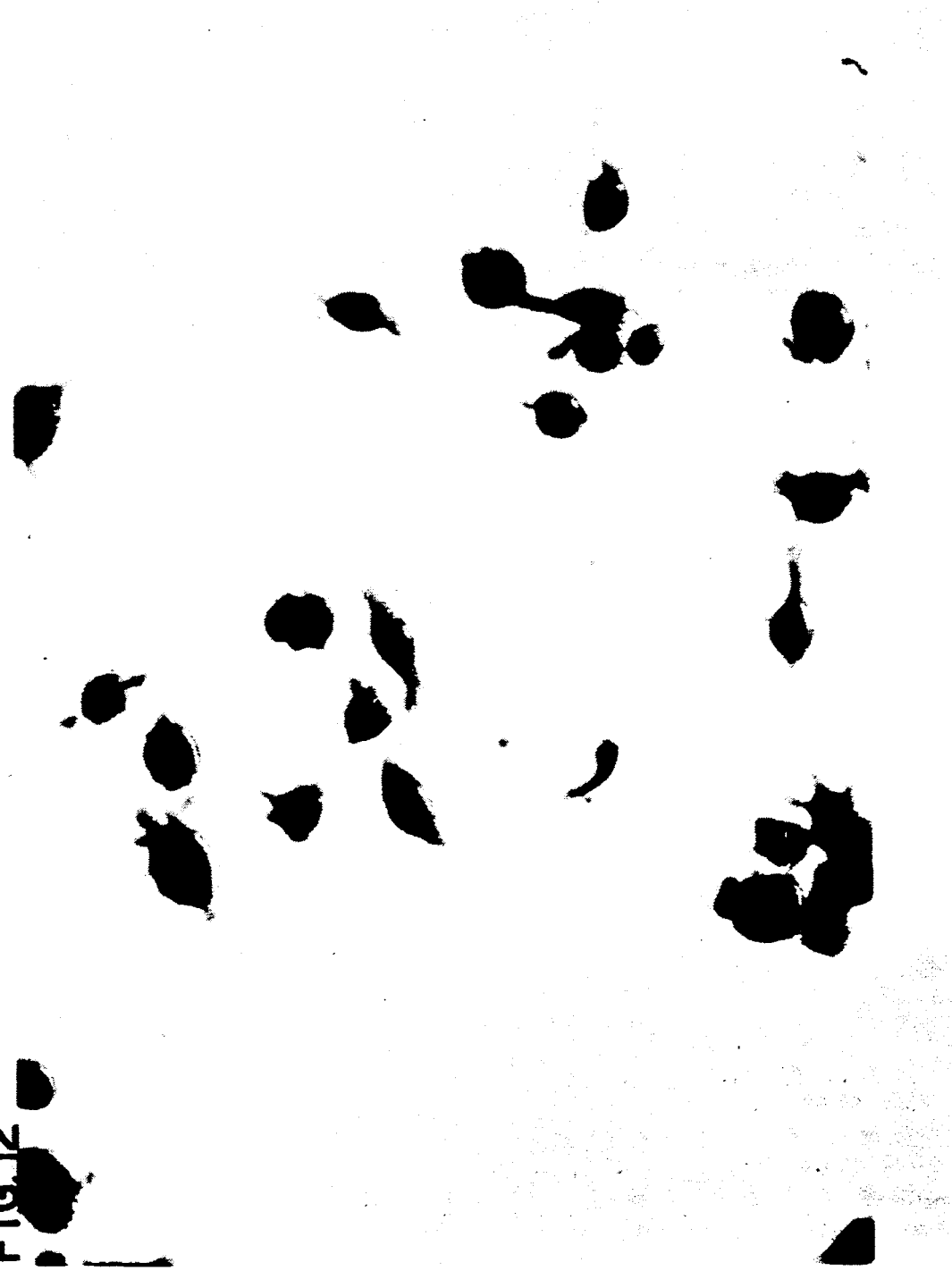
FIG. 12 shows human HT-1080 fibrosarcoma cell spreading on a plastic surface coated with synthetic peptide R38 derived from the A chain of laminin.
Figure 14:
FIG. 14 shows human HT-1080 fibrosarcoma cell spreading on a plastic surface coated with B1 chain peptide F-11 (negative control).
Figure 15:
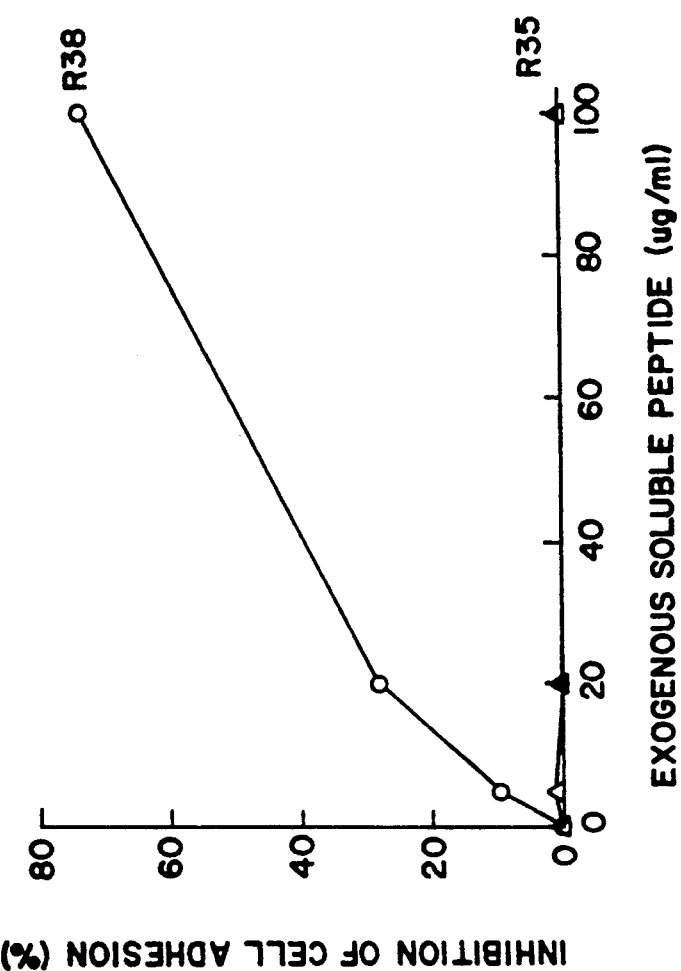
FIG. 15 shows inhibition of laminin-mediated HT-1080 human fibrosarcoma cell adhesion by laminin A chain peptides.

FIGS. 5, 13 and 14 provided control comparisons for HT-1080 cell spreading evaluation.

A number of practical applications for the polypeptides of the present invention can be envisioned. Such applications include the promotion of the healing of wounds caused by the placement of synthetic substrata within the body. Such synthetic substrata can include artificial vessels, intraocular contact lenses, hip replacement implants and the like, where cell adhesion is an important factor in the acceptance of the synthetic implant by normal host tissue. In addition, the polypeptides could be used for the delivery of heparin-binding molecules (e.g., growth factors or anti-coagulants).

As described in U.S. Pat. No. 4,578,079, medical devices can be designed making use of these polypeptides to attract cells to the surface in vivo or even to promote the growing of a desired cell type on a particular surface prior to grafting. An example of such an approach is the induction of endothelial cell growth on a prosthetic device such as a blood vessel, heart valve or vascular graft, which is generally woven or knitted from nitrocellulose or polyester fiber, particularly Dacron TM (polyethylene terephthalate) fiber. Most types of cells are attracted to laminin and to the present polypeptides. The latter point indicates the potential usefulness of these defined polypeptides in coating a patch graft or the like for aiding wound closure and healing following an accident or surgery. The coating and implantation of synthetic polymers may also assist in the regeneration of nerves following crush traumae (e.g., spinal cord injuries) or after angioplasty.

In such cases, it may be advantageous to couple the peptide to another biological molecule, such as collagen, a glycosaminoglycan or a proteoglycan. It is also indicative of their value in coating surfaces of a prosthetic device which is intended to serve as a temporary or semipermanent entry into the body, e.g., into a blood vessel or into the peritoneal cavity, sometimes referred to as a percutaneous device. Such devices include controlled drug delivery reservoirs or infusion pumps.

Laminin can effectively promote the growth and differentiation of diverse cell types. Also, the polypeptides of the present invention can be used to promote cell adhesion of various cell types to naturally occurring or artificial substrata intended for use in vitro. For example, a culture surface such as the wells of a microtiter plate or the medium contacting surface of microporous fibers or beads, can be coated with the cell-attachment polypeptides.

As one example of commercial use of cell - attachment surfaces, Cytodex 3 ® microcarriers, manufactured by Pharmacia, are dextran-based microspheres coated with denatured collagen, making it possible to grow the same number of adherent cells in a much smaller volume of medium than would be possible in dishes. The activity of these beads is generally dependent upon the use of coating protein in the growth medium and the present polypeptides are expected to provide an improved, chemically-defined coating for such purposes. Other surfaces or materials may be coated to enhance attachment, such as glass, agarose, synthetic resins or long-chain polysaccharides.

In the past, selected laminin domains have been studied for ability to decrease the metastatic potential of invasive cell lines [McCarthy et al., *J. Natl. Cancer Inst.*, 80, 108–116 (1988)]. This effect is mediated via the saturation and therefore neutralization of cell surface receptors for laminin. In accordance with the present invention, the data presented herein suggest that receptors for the polypeptides derived from the G domain of the A chain of laminin should exist on cell surfaces of malignant cells. Consequently, these polypeptides could be used to block laminin receptors of metastatic cells and therefore reduce their metastatic potential.

The invention has been described with reference to various specific and preferred embodiments and techniques. However, it should be understood that many variations and modifications may be made while remaining within the spirit and scope of the invention.

What is claimed is:

1. A polypeptide having a sequence of at least about 5 amino acids corresponding to an amino acid sequence within the G domain of the A chain of laminin, wherein said polypeptide promotes cell adhesion.

2. The polypeptide of claim 1 wherein said polypeptide promotes cell spreading.

3. The polypeptide of claim 2 wherein said polypeptide exhibits cell adhesion capacity.

4. A polypeptide according to claim 1 having the formula:
lys-gln-asn-cys-leu-ser-ser-arg-ala-ser-phe-arg-gly-cys-val-arg-asn-leu-arg-leu-ser-arg.

5. A polypeptide according to claim 1 having the formula:
gly-arg-leu-his-phe-met-phe-asp-leu-gly-lys-gly-arg-thr-lys-val-ser-his-pro.

6. A polypeptide according to claim 1 having the formula:
gly-thr-lys-asp-phe-leu-ser-iso-glu-leu-val-arg-gly-arg-val-lys-val-met-val-asp.

7. A polypeptide according to claim 1 having the formula:
his-ser-iso-ser-leu-val-arg-asn-arg-arg-val-iso-thr-iso-gln.

8. A polypeptide according to claim 1 having the formula:
lys-ala-thr-pro-met-leu-lys-met-arg-thr-ser-phe-his-gly-cys-iso-lys.

9. A polypeptide according to claim 1 having the formula:
lys-glu-gly-tyr-lys-val-arg-leu-asp-leu-asn-iso-thr-leu-glu-phe-arg-thr-thr-ser-lys.

10. A polypeptide having a sequence of at least about 5 amino acids corresponding to an amino acid sequence within the G domain of the A chain of laminin, wherein said polypeptide promotes heparin binding.

11. A polypeptide having the formula:
lys-gln-asn-cys-leu-ser-ser-arg-ala-ser-phe-arg-gly-cys-val-arg-asn-leu-arg-leu-ser-arg.

12. A polypeptide having the formula:
gly-arg-leu-his-phe-met-phe-asp-leu-gly-lys-gly-arg-thr-lys-val-ser-his-pro.

13. A polypeptide having the formula:
gly-thr-lys-asp-phe-leu-ser-iso-glu-leu-val-arg-gly-arg-val-lys-val-met-val-asp.

14. A polypeptide having the formula:
his-ser-iso-ser-leu-val-arg-asn-arg-arg-val-iso-thr-iso-gln.

15. A polypeptide having the formula:
lys-ala-thr-pro-met-leu-lys-met-arg-thr-ser-phe-his-gly-cys-iso-lys.

16. A polypeptide having the formula:
lys-glu-gly-tyr-lys-val-arg-leu-asp-leu-asn-iso-thr-leu-glu-phe-arg-thr-thr-ser-lys.

17. A prosthetic device designed for placement in vivo, comprising a surface coated with a composition comprising a polypeptide having a formula of lys-gln-asn-cys-leu-ser-ser-arg-ala-ser-phe-arg-gly-cys-val-arg-asn-leu-arg-leu-ser-arg or gly-arg-leu-his-phe-met-phe-asp-leu-gly-lys-gly-arg-thr-lys-val-ser-his-pro or gly-thr-lys-asp-phe-leu-ser-iso-glu-leu-val-arg-gly-arg-val-lys-val-met-val-asp or his-ser-iso-ser-leu-val-arg-asn-arg-arg-val-iso-thr-iso-gln or lys-ala-thr-pro-met-leu-lys-met-arg-thr-ser-phe-his-gly-cys-iso-lys or lys-glugly-tyr-lys-val-arg-leu-asp-leu-asn-iso-thr-leu-glu-phe-arg-thr-thr-ser-lys.

18. The prosthetic device of claim 17, wherein said surface is made of a synthetic resin fiber.

19. The prosthetic device of claim 17, wherein said surface constitutes a portion of an intraocular contact lens.

20. A prosthetic device in accordance with claim 18, wherein said synthetic resin fiber is selected from the group consisting of nitrocellulose or polyester.

21. A prosthetic device in accordance with claim 18, wherein said synthetic resin fiber is a polyethylene terephthalate.

* * * * *

UNITED STATES PATENT AND TRADEMARK OFFICE
CERTIFICATE OF CORRECTION

PATENT NO. : 5,266,328
DATED : November 30, 1993
INVENTOR(S) : Amy P. N. Skubitz et al.

It is certified that error appears in the above-identified patent and that said Letters Patent is hereby corrected as shown below:

At column 1, line 48, for "Pat." read --Path.--

At column 6, in Table I, after the subheading "Net Charge" insert --±--

At column 7, in Table I, after the subheading "Net Charge" insert --±--

At column 7, in Table I, line 9 of the footnotes, for "intelliGenetics" read --IntelliGenetics--

At column 12, in Table IV, for the subheading "For Heparin Binding" read --Poor Heparin Binding--

Signed and Sealed this

Twentieth Day of February, 1996

Attest:

BRUCE LEHMAN

Attesting Officer

Commissioner of Patents and Trademarks